United States Patent [19]

Yamanoi et al.

[11] Patent Number: 4,851,284
[45] Date of Patent: Jul. 25, 1989

[54] ABSORBENT ARTICLE

[75] Inventors: Akira Yamanoi; Daisuke Shiba, both of Utsunomiya, Japan

[73] Assignee: Kao Corporation, Tokyo, Japan

[21] Appl. No.: 53,014

[22] Filed: May 22, 1987

[30] Foreign Application Priority Data

May 22, 1986 [JP] Japan .................................. 61-117949

[51] Int. Cl.⁴ .............................................. D02G 3/00
[52] U.S. Cl. .................................... 428/284; 428/221; 428/224; 428/288; 428/296; 428/297; 428/298; 428/373; 428/913
[58] Field of Search ............... 428/913, 284, 224, 221, 428/288, 373, 296, 297, 298

[56] References Cited

U.S. PATENT DOCUMENTS

| | | | |
|---|---|---|---|
| 4,392,861 | 7/1983 | Butterworth | 428/286 |
| 4,421,813 | 12/1983 | Athey | 428/373 |
| 4,480,000 | 10/1984 | Watanabe | 428/284 |
| 4,508,113 | 4/1985 | Maloney | 428/287 |
| 4,522,203 | 6/1985 | Mays | 428/287 |
| 4,555,430 | 11/1985 | Mays | 428/373 |
| 4,592,943 | 6/1986 | Cancian et al. | 428/373 |
| 4,652,484 | 3/1987 | Shila et al. | 428/373 |
| 4,737,404 | 4/1988 | Jackson | 428/373 |

FOREIGN PATENT DOCUMENTS 2114895  9/1983  United Kingdom .

Primary Examiner—James J. Bell
Attorney, Agent, or Firm—Birch, Stewart, Kolasch & Birch

[57] ABSTRACT

An absorbent article comprises a non-woven fabric comprising on a surface area thereof conjugate fibers comprising a first resin and a second resin having a melt flow rate of 10 to 50, the first resin having a higher melting point by at least 100° C. than the second.

18 Claims, 1 Drawing Sheet

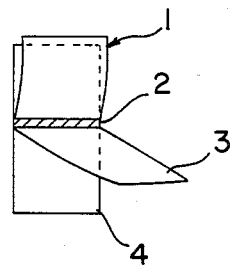
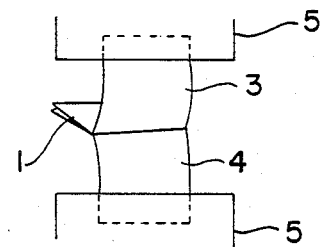
FIG. 1          FIG. 2
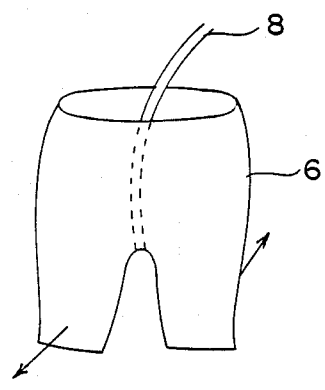
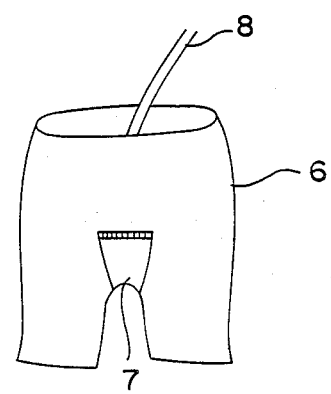
FIG. 3          FIG. 4

ABSORBENT ARTICLE

BACKGROUND OF THE INVENTION

1. Field of the invention.

The present invention relates to a disposable absorbent article excellent in absorbency, and particularly to a sanitary napkin, paper diaper, toilet sheet or the like, characterized in that a non-woven fabric excellent in thermoprocessability is used as its surface material.

2. Description of the Related Art

The absorbent article according to the prior art, for example, a sanitary napkin or paper diaper, fundamentally comprises an absorbent layer made of cottony pulp, absorbent paper or the like, a leakproof layer attached to the bottom and the sides of the absorbent layer and a non-woven fabric covering the surface.

Recently, technology has rapidly advanced to develop new materials for an absorbent article, for example, a highly absorbent polymer or non-woven fabric made of synthetic fibers by a dry process, thus remarkably enhancing the absorbency of such an article. However, even an absorbent article constituted by materials each having excellent absorbency does not always exhibit sufficient performance, when practically used, which is apparent from the fact that the greatest complaint as yet of consumers against such an absorbent article is leakage from the crotch.

The greatest reason for the leakage is that the movement of the crotch of a wearer gives irregular stress to the absorbent article so as to cause separation of materials constituting the article or significant twist or wrinkle of the article. Among them, the non-woven fabric is in direct contact with the skin of a wearer and therefore is seriously stressed, so that the fabric frequently tends to be separated from a leakproof layer or an absorbent layer. Therefore, it has been expected that the fabric and these layers be unified by some method or other.

It is possible that a non-woven fabric is adhesive-bonded to a leakproof layer or an absorbent layer with a pressure-sensitive adhesive or a hot-melt adhesive to thereby unify both. However, this process necessitates complicated steps which result in prominently enhanced production cost.

A process which comprises melting a non-woven fabric by simple hot-pressing and bonding the melted fabric to the object, a so-called heat bonding process, if possible, allows high-speed production of the article without necessitating complicated steps and results in only slight enhancement in cost.

It can be understood from the above description that a non-woven fabric excellent in thermoprocessability is necessary for enhancing the leakproofness of an absorbent article, particularly under dynamic conditions. However, the non-woven fabric according to the prior art is quite insufficient in thermoprocessability. The problems of the non-woven fabric of the prior art can be broadly divided into the following three groups.

The first problem is that the meltability of a non-woven fabric is insufficient. This problem can further be resolved into two cases. In the first case, a non-woven fabric is made of fibers which can not be melted by heating, for example, rayon or acrylic fiber, so that the non-woven fabric can not be bonded to the object by melting at all. In the other case, a nonwoven fabric is made of a fiber which has a high melting point to exhibit insufficient fluidity even when melted, for example, polyester or nylon fiber, so that the processing temperature does not fall in a suitable range and the bond strength of the fabric to the object is low.

The second problem is that the melted non-woven fabric adheres to a heat sealer, so that the fabric is broken in the heat-bonded area or a processing machine is damaged. With the purpose of overcoming the above first problem, the blending of a low-melting fiber in a non-woven fabric has been carried out. However, in most cases, the fiber comprises components having the same melting point or components having melting points slightly different from each other like polyethylene/polypropylene conjugate fiber. Such fiber has a narrow melting point range, so that the whole of the fiber tends to be melted simultaneously in the thermoprocessing even by the slight deflection in processing temperature and the melted fiber is transferred to a sealer in a moment so that the processing machine is damaged and the fabric is broken in the heat-bonded area. The larger the content of such a low-melting fiber in a non-woven fabric, the more significant this problem. On the contrary, in the case wherein the content of a low-melting fiber in a non-woven fabric is low, even when the whole of the low-melting fiber is melted by heating, the melted fiber is prevented from transferring to a sealer to some extent in the temperature range wherein a high-melting fiber is maintained in a state of fiber, because the bonding or interlocking of the melted low-melting fiber to the high-melting fiber serves to prevent such transfer. However, the heat bonding effect is insufficient, because the content of a low-melting fiber is low. Additionally, the melted fiber still transfers to a sealer to some extent, so that neither breaking of a non-woven fabric in the heat-bonded area nor damage to a processing machine due to the melted fiber built up on the sealer, particularly by prolonged operation, can be substantially prevented.

The third problem is that it is difficult to produce a non-woven fabric having thermoprocessability and strength which are well-balanced with each other, while the strength is a basic physical property of a non-woven fabric. Recently, a non-woven fabric produced by dry heat-bonding process and excellent in strength, touch and absorbency has been frequently used as a material for a disposable sanitary article such as sanitary napkin or paper diaper. The non-woven fabric produced by this process has a structure wherein fiber webs are fixed to each other by the heat-bonding between fibers themselves and therefore generally contains a low-melting fiber such as polyolefin at a high content. Such a non-woven fabric can not exhibit sufficient thermoprocessability, as described in the above description of the second problem. In order to improve the thermoprocessability of such a non-woven fabric a method which is reverse to that for improving the first problem has been carried out. That is to say, the blending of a high-melting fiber has been carried out to thereby improve the thermoprocessability to some extent.

However, a non-woven fabric prepared by this method has not only the problems indicated in the description of the second problem but also a disadvantage in that the bonding or interlocking between the two fibers is insufficient, so that the non-woven fabric exhibits a lowered strength and causes unnegligible fuzzing in some uses. Further, when such a non-woven fabric is produced by the thermal treatment under severe conditions for the purpose of enhancing the strength, the obtained fabric is rigid and exhibits lowered touch so that the excellent balance among the strength, touch and anti-fuzzing properties which is an advantage inherent to a non-woven fabric produced by dry heat-bonding process is detracted.

As described above, the non-woven fabric according to the prior art has disadvantages in that the thermoprocessing thereof is difficult and that it is very difficult to well-balance the thermoprocessability with the strength. Therefore, no absorbent article excellent in leakproofness has been produced as yet.

SUMMARY OF THE INVENTION

The inventors of the present invention have investigated to develop a non-woven fabric which is excellent in thermoprocessability and the basic requirements, i.e., strength and anti-fuzzing properties, of which can be each controlled over a wide range and have accomplished the present invention.

The present invention relates to an absorbent article wherein a non-woven fabric containing a conjugate fiber in at least part of the surface layer thereof is used as its surface material, said conjugate fiber comprising two resin components, one of which (the first component) has a melting point higher than that of the other component (the second component) by at least 100° C. and the second component of which exhibits a melt flow rate of 10 to 50 when melted.

With regard to the above first and second problems, the non-woven fabric to be used in the absorbent article according to the present invention must satisfy at least the following requirements with respect to thermoprocessability.

An absorbent article of the invention comprises a non-woven fabric comprising on a surface area thereof conjugate fibers comprising a first resin and a second resin having a melt flow rate of 10 to 50, the first resin having a higher melting point by at least 100° C. than the second.

It is preferable that the first resin has a melting point of 200° C. or higher and the second resin has a melting point of 180° C. or lower, a weight ratio of the first resin to the second resin in the conjugate fibers ranges from 70/30 to 30/70 and 10 to 100 percent of said non-woven fabric has been formed from the conjugate fibers on the surface thereof.

It is best that all the surface area of the non-woven fabric has been formed from the conjugate fibers.

A practical embodiment of the invention article may comprise the above shown non-woven fabric, a leak-proof material and an absorbent such as an absorbent polymer and fluff pulp. The article is improved in that the non-woven fabric cannot slip out of on the leak-proof material, but is fixed thereon. In order to assure this feature, the non-woven fabric and the leak-proof material are partialy fastened on each other. The fastening is effected by fusing the thermoplastic resin contained in the conjugate fibers. For example, the absorbent is wrapped with the leak-proof sheet, except for the top surface, and an assembly of the absorbent and the leak-proof sheet is enveloped with the non-woven fabric. In the obtained article, the leak-proof sheet at the ends extending up to the top surface of the absorbent and the non-woven fabric are fixed on each other. Alternatively both are fixed on each other at a portion of the back side so as not to contact the skin of a user.

The first requirement is that at least part of non-woven fabric can be melted by hot pressing to thereby effectively bond the fabric to the object. This is apparent from the object of the present invention. The second requirement is that the fabric melted by hot pressing is not transferred to a sealer. The third requirement is that the above two requirements be satisfied over a wide temperature range. Particularly, the second and third requirements are very important for attaining stable thermoprocessing in the practical production of the absorbent article.

The inventors of the present invention have examined on these requirements in more detail and have found that the requirements can be satisfied by the means which will further be described below.

BRIEF DESCRIPTION OF THE DRAWINGS

FIG. 1 is a perspective view of a sample for measuring the bond strength.

FIG. 2 is a perspective view showing the state of the sample in the measurement.

FIG. 3 is a perspective view of a mobile model of a woman's waist for the measurement of the absorption capacity under a dynamic condition.

FIG. 4 is a view showing the state of the sample set on the model. 1 . . . test piece, 2 . . . sealed area, 3 . . . non-woven fabric, 4 . . . laminated paper, 5 . . . chuck, 6 . . . mobile model of woman's waist, 7 . . . test sample, 8 . . . tube

DETAILED DESCRIPTION OF THE INVENTION

First, it is necessary for effectively bonding non-woven fabric to the object that the non-woven fabric must contain a component which can be melted by hot-pressing and, transferred to the object by speedy melt flow. The second resin component constituting the conjugate fiber according to the present invention is used for this purpose and therefore must exhibit a melt flow rate of 10 to 50, the melt flow rate being an indication of fluidity of a melt. The higher the melt flow rate of the second resin component, the higher the fluidity of the melt, which is preferable for heat bonding. Particularly, when the melt flow rate of the second resin component is 20 or above, an absorbent article can be produced with a short hot-pressing time at a high productivity rate, which is effective particularly in the production of a disposable article. However, when the melt flow rate of the second resin component is too high, the adhesion of fibers to each other of the resulting non-woven fabric is lowered, which is particularly remarkable when the non-woven fabric is produced by a heat-bonding process. Accordingly, the melt flow rate of the second resin component must not exceed 50 so as not to lower the strength of the fabric.

Next, a process for preventing the transfer of a non-woven fabric to a sealer and the breaking of the non-woven fabric in the bonded area will be described. For this purpose, not all of the fiber must be melted. Therefore, a conjugate fiber may be used, which comprises the second resin component which is melted by hot-pressing to give a melt exhibiting a suitable fluidity and the first resin component which is not melted to be maintained in a fibrous state as a whole and serve as a skeleton of the non-woven fabric. It is necessary for attaining such effects in the practical production with scattering in heat-bonding temperature and line rate that the difference in melting point between the first resin component and the second one must be at least 100° C. Further, the higher the melting point of the first resin component, the wider the possible thermoprocessing temperature range of the non-woven fabric. Furthermore, it is necessary for overcoming the first and second problems simultaneously that such a conjugate fiber comprising the first resin component and the second resin component is contained in at least part of the surface layer of the non-woven fabric. It is still preferable that such a conjugate fiber is contained in the surface layer of the non-woven fabric in a context of 10% by weight or above in order to further enhance the bond strength. The higher the content of the conjugate fiber in the surface layer, the higher the bond strength and the more excellent the thermoprocessability of the non-woven fabric, while neither breaking in the heat-bonded area nor adhering of the melted component to a sealer is caused.

The non-woven fabric to be used in the absorbent article according to the present invention can satisfy the third requirement, if it can be melted at a temperature as low as possible and does not adhere to a sealer until a temperature as high as possible. That is to say, it is preferable that the first resin component of the conjugate fiber according to the present invention has a melting point as high as possible, while the second resin component thereof has a melting point as low as possible. It is still preferable that the melting point of the former is not lower than 200° C. and that of the latter is not higher than 180° C.

A process for overcoming the third problem mentioned above will now be described.

A non-woven fabric produced by a dry heat-bonding process contains a low-melting fiber in a high ratio so that it is not problematic in the heat-bonding power to the object. Accordingly, the thermoprocessability of this non-woven fabric can be enhanced by preventing the breaking thereof in the bonded area or reducing the adhering thereof to a sealer. As described above, it is necessary for this purpose that the non-woven fabric contains a high-melting fiber having a melting point higher than that of the binder fiber. Further, it is necessary that the high-melting fiber also serves as a binder fiber to thereby reduce the lowering in the strength or the fuzzing. Thus, the use of the conjugate fiber according to the present invention is very effective for this purpose. Furthermore, it is necessary for enhancing the thermoprocessability of a nonwoven fabric produced by a dry heat-bonding process that the conjugate fiber according to the present invention is contained at least in the surface layer of the fabric, preferably in a content of 10% by weight or above. Particularly, with the purpose of attaining the excellent thermoprocessability substantially free from the above-mentioned first and second problems, at least 50% by weight, preferably the whole of the binder fiber constituting the non-woven fabric may be replaced with the conjugate fiber according to the present invention.

The conjugate fiber according to the present invention may be any one, as far as it satisfies the above requirements. Examples of the combination of the first resin component with the second resin component include polyacrylonitrile/polyolefin, polyester/polyolefin, polyamide/polyolefin, polyacrylonitrile/ethylenevinyl acetate copolymer, polyester/ethylene-vinyl acetate copolymer and polyamide/ethylene-vinyl acetate copolymer. Among them, polyester/polyolefin and polyester/ethylene-vinyl acetate copolymer are preferable from the standpoint of heat-bonding power, thermoprocessability and cost. Further, although examples of the polyolefin to be used as the second resin component include polypropylene, low-density polyethylene, medium-density polyethylene and high-density polyethylene, polypropylene and high-density polyethylene exhibiting a melting point of at least 130° C. are particularly preferred in the use of sanitary napkin, paper diaper, toilet sheet or the like and between the both, the latter is still preferred because of its lower melting point, the reasons for which will be described hereinbelow.

The structure of the conjugate fiber comprising the first resin component and the second resin component may be a so-called core-sheath structure comprising a core made of the first resin component and a sheath made of the second resin component, a so-called sea-island structure wherein very fine filaments made of the first resin component are dispersed in the second resin component or other structure.

Although the ratio of the first resin component to the second resin component in the conjugate fiber according to the present invention is not particularly limited, the content of the second resin component is preferably 30 to 70% by weight.

Although the non-woven fabric according to the present invention can be effectively applied to various uses wherein thermoprocessing is indispensable, application thereof to a disposable absorbent article such as sanitary napkin, paper diaper, toilet sheet or the like and requirements for this application will particularly be described below.

The non-woven fabric to be used in such a disposable absorbent article must exhibit strength, touch and absorbency satisfactory for practical use and can be thermally processed at a high rate.

First, the touch of the non-woven fabric which is influenced by thermoprocessing will be described. With respect to the above absorbent article, the object to which the non-woven fabric is heat-bonded is different depending the area of the article to be thermally processed. When thermoprocessing is applied to the working surface (skin-contacting surface) of the absorbent article, the non-woven fabric is generally bonded to an absorbent paper placed under the fabric, while when thermoprocessing to the working surface is avoided, the fabric is generally bonded to a leakproof paper covering the bottom and the both sides of the absorbent layer. However, the heat-bonding strength between the non-woven fabric and a paper is generally low, so that a higher thermoprocessing temperature is required to enhance the heat-bonding strength. Further, such a higher-temperature processing tends to bring the non-woven fabric into a filmy state to give a rigid and touch-poor bonded area. On the other hand, the leak-proof paper is generally laminated with a film and the bond strength of the non-woven fabric to the laminated leak-proof paper is so high that a sufficient high bond strength can be attained by selecting suitable processing conditions without lowering the touch. Accordingly, in the production of the above absorbent article wherein great importance is attached to the touch to the skin, the heat-bonding of the non-woven fabric to the laminated leakproof paper is more effective than the heat-bonding thereof to the absorbent paper of the working surface.

Further, when an absorbent article having more excellent touch is desired, the thermoprocessing is preferably carried out at a temperature as low as possible to thereby prevent the non-woven fabric from being brought into a filmy state as completely as possible. In some case, the thermoprocessing temperature must be controlled at a temperature near the melting point of the non-woven fabric. In this case, it is effective in attaining a constant heat-bonding strength which hardly varies by the scattering of the thermoprocessing temperature in the practical production that the melting point of the film is lower than that of the non-woven fabric. The laminating film generally has a melting point of about 100° to 120° C. Therefore, it is preferable that a non-woven fabric having a melting point of 130° C. or above is used to thereby stabilize the thermoprocessing and allow the selection of a laminating film from a wide range. For these reasons, it is the most desirable that the second resin component constituting the conjugate fiber is high-density polyethylene.

From the standpoint of the balance between the strength of the non-woven fabric and the touch thereof, it is preferred that at least the surface layer of the non-woven fabric comprise 50 to 100% by weight of the conjugate fiber according to the present invention and 50 to 0% by weight of a fiber having a melting point near that of the first resin component of the conjugate fiber. The preferable basis weight of the non-woven fabric to be used in a sanitary napkin is 10 to 30 g/m² as a whole and 5 to 15 g/m² with respect to the surface layer thereof, while the one to be used in a paper diaper is 20 to 50 g/m² as a whole and 7 to 20 g/m² with respect to the surface layer thereof. Further, it is preferable that the non-woven fabric to be used in these articles has a basis weight as low as possible and an elasticity as high as possible. Accordingly, the use of high-density polyethylene as the second resin component constituting the conjugate fiber according to the present invention is the most desirable in this regard, because high-density polyethylene exhibit high heat-bonding power and is rich in rigidity. Although the fineness of the conjugate fiber may be 1.5 to 10 denier, it is preferably 1.5 to 6 denier in respect of the balance between strength and touch.

Finally, an absorbent article is required to exhibit suitable absorbency. Therefore, it is preferred that a hydrophilic nature is imparted to at least the surface of the above conjugate fiber to thereby make the non-woven fabric suitably hydrophilic. Examples of the process for imparting a hydrophilic nature to the surface of the conjugate fiber include treatment of the surface of the conjugate fiber with a surfactant, chemical modification of the surface with a compound having a hydrophilic group such as a monomer having a hydrophilic group or polymer thereof, plasma treatment and physical modification of the surface with a compound having a hydrophilic group by incorporation or the like. The chemical modification may be carried out either by chemically bonding a compound having a hydrophilic group to the surface of the conjugate fiber or by covering the surface with a product formed by the crosslinking of such compounds with each other. As described above, a hydrophilic nature is generally imparted to the surface of the conjugate fiber in the fiber-producing step. However, after the production of the non-woven fabric, the fabric may be subjected to the above chemical or physical modification or the treatment with a surfactant solution to thereby impart a hydrophilic nature to the surface of the conjugate fiber.

The absorbent article according to the present invention wherein the above non-woven fabric and other constituent member are unified by thermoprocessing will be further described in more detail by the following Examples.

EXAMPLES 1 TO 15 AND COMPARATIVE EXAMPLES 1 TO 9

Fiber, Non-woven Fabric and Absorbent Article

The fibers used in Examples as a conjugate fiber according to the present invention and those used in Comparative Examples as a fiber not according to the present invention are shown in Table 1.

Physical properties of the non-woven fabrics each produced from the above fiber and physical properties of the absorbent articles each produced by using the non-woven fabric according to the present invention or the comparative one not according to the present invention are shown in Tables 2 and 3.

Table 2 shows the data with respect to the non-woven fabrics having the first and second problems described in the above Description of the Related Art and those free from these problems, while Table 3 shows the data with respect to the non-woven fabrics having the third problem described above and those wherein the problem is solved.

In Examples 1 to 3, 8, 10 to 15 and Comparative Examples 1, 2 and 6 to 9, the non-woven fabric was produced by using the conjugate fiber as a binder fiber according to the heat-bonding process which comprises passing hot air of 140° C. (170° C. in Example 9 only) through card webs to fusion-bond and fix the ES fiber to other fibers. The non-woven fabric used in Comparative Example 7 is commercially available PET spun bond non-woven fabric. Further, in Examples 4 to 7 and 9 and Comparative Examples 3 to 5, the non-woven fabric was produced by exposing the webs to high-pressure water with a jet pressure of 55 kg/cm² to cause the interlocking of the fiber.

The absorbent article was produced by replacing the non-woven fabric of a commercially available sanitary napkin under the trade name of Rorie from Kao Corporation with the non-woven fabric shown in Table 2 or 3 and subjecting the resulting napkin to sealing which will be described below.

Test Method for Fiber and Non-woven Fabric

With respect to the fibers shown in Table 1, melting points of the first and second resin components and melt flow rate of the second resin component were measured. Among items of Tables 2 and 3, tensile strength and falling out of fuzz are with respect to the non-woven fabric, while bond strength and state of bonded area are with respect to the absorbent articles after the sealing. Further, the absorbent article was examined for absorption capacity under a dynamic condition.

(1) Melting Point

The fibers shown in Table 1 were examined for melting point according to the following method.

A temperature at which a maximum heat absorption of a fiber sample is observed was determined with a DSC by increasing the temperature of the sample fiber at a rate of 10° C. per minute and this temperature was regarded as the melting point of the sample fiber.

(2) Melt Flow Rate (MFR)

The second resin components shown in Table 1 were examined for melt flow rate according to the following method.

The MFR of the second resin component can be determined after the removal of the first resin component from the conjugate fiber by some method or other. With respect to SH-1 to 6 and SP-4, the polyester component was removed according to the method of JIS L 1030-1977. With respect to MBF, only the second resin component was separated out in the spinning step. The second resin component thus separated was examined for weight (gram) of a sample flowing out of a melt indexer at a temperature higher than the melting point of the component by about 30° C. per 10 minutes and this weight (gram) was regarded as the MFR of the sample.

Test temperature:
150° C. when the second resin component is polyethylene
180° C. when the second resin component is polypropylene Test load: 2160 g

(3) Tensile Strength

The breaking strength of a non-woven fabric sample having a width of 50 mm was determined by stretching it with a width of 150 mm and a stretching rate of 300 mm/min and regarded as the tensile strength of the sample. In this test, the direction of orientation of the fibers constituting the non-woven fabric sample was the widthwise direction of the sample.

(4) Falling Out of Fuzz

A non-woven fabric was rubbed with a sponge loaded at 15 g/cm$^2$ and the amount of fiber adhering to the non-woven fabric was determined and evaluated according to the following criteria:
3 ... falling out of fiber was hardly observed
2 ... falling out of fiber was unnegligible but no pill was observed
1 ... falling out of fiber was significant and many pills were observed

(5) Sealability

The absorbent articles shown in Tables 2 and 3 were each produced by sealing the non-woven fabric with a leakproof paper (low-density polyethylene-laminated paper) under the following condition. The sealing was carried out with a heat sealer, while transferring the absorbent article at a line rate of 120 m/min. The sealing width was 2.5 mm. The articles shown in Table 2 were each produced by sealing at a constant temperature of 200° C. and examined for bond-strength and state of bonded area, excepting Examples 10 and 11 wherein sealing was carried out at a temperature near the melting point of the second resin component of the conjugate fiber contained in the non-woven fabric. On the other hand, with respect to the articles shown in Table 3 the sealing was carried out at various temperature to determine the temperature range wherein effective bonding (corresponding to the state of bonded area of rank 2 or 3) is attained.

(6) Bond Strength

A sample of the absorbent article after the sealing was cut to obtain a test sample 1 containing a sealed area 2 and having a width of 30 mm as shown by FIG. 1. This test sample 1 was catched by chucks 5 at the end of a non-woven fabric 3 and that of a laminated paper 4 and the chucks 5 were stretched in opposite directions to each other to determine the maximum peeling load. The maximum load was regarded as the bond strength of the sample.

(7) State of Bonded Area

The sealed area was observed with the naked eyes and evaluated according to the following criteria:
3 ... neither breaking of the bonded area nor adhering to a sealer was observed.
2 ... breaking and imperfect bonding were observed in part of the bonded area, but no adhering to a sealer was observed.
1 ... breaking of the bonded area and adhering to a sealer were too significant to carry out the heat bonding.

(8) Absorption Capacity Under Dynamic Condition

As shown by FIG. 4, a test sample 7 was set on a mobile model 6 of a woman's waist as shown by FIG. 3. After the initiation of the walking of the model, a test liquid was poured into the sample 7 via a tube 8 at a rate of 15 g/min, while continuing the walking. The amount of the test liquid poured until the leakage of the liquid was observed was determined and regarded as the absorption capacity of the sample under a dynamic condition. The higher the absorption capacity under a dynamic condition, the higher the leakproofness.

TABLE 1

| Fiber | Abbreviation | Maker | First component Composition | Melting point, °C. | Second component Composition | Melting point, °C. | MFR |
|---|---|---|---|---|---|---|---|
| NBF(SH)-1 | SH-1 | Daiwa Spinning Co., Ltd. | polyester | 268 | high-density polyethylene | 133 | 8 |
| NBF(SH)-2 | SH-2 | Daiwa Spinning Co., Ltd. | polyester | 268 | high-density polyethylene | 133 | 17 |
| NBF(SH)-3 | SH-3 | Daiwa Spinning Co., Ltd. | polyester | 268 | high-density polyethylene | 133 | 25 |
| NBF(SH)-4 | SH-4 | Daiwa Spinning Co., Ltd. | polyester | 268 | high-density polyethylene | 133 | 35 |
| NBF(SH)-5 | SH-5 | Daiwa Spinning Co., Ltd. | polyester | 268 | high-density polyethylene | 133 | 57 |
| NBF(SH)-6 | SH-6 | Daiwa Spinning Co., Ltd. | polyester | 268 | medium-density polyethylene | 123 | 35 |
| NBF(SP)-4 | SP-4 | Daiwa Spinning Co., Ltd. | polyester | 268 | polyethylene | 161 | 38 |
| NBF(H) | NBF | Daiwa Spinning Co., Ltd. | polypropylene | 161 | polyethylene | 133 | 23 |
| PET | PET | Teijin Limited | polyester | 268 | | | |

TABLE 2

| No. of Ex. or Comp. Ex. | Fixing process of web | Basis weight (g/m²) | Fiber | Surface layer Fineness (denier) | Content (%) | Fiber | Inside layer Fineness (denier) | Content (%) | Tensile strength (g/50 mm) | Falling out of fuzz (rank) | Bond strength (g/30 mm) | State of bonded area (rank) | Absorption capacity under dynamic condition (g) | Processing temperature (°C) |
|---|---|---|---|---|---|---|---|---|---|---|---|---|---|---|
| Comp. Ex. 1 | heat bonding | 20 | SH-1 | 2 | 100 | SH-1 PET | 3 6 | 50 50 | 325 | 3 | 22 | 3 | 4.9 | 200 |
| Ex. 1 | heat bonding | 20 | SH-2 | 2 | 100 | SH-2 PET | 3 6 | 50 50 | 283 | 3 | 101 | 3 | 7.6 | 200 |
| Ex. 2 | heat bonding | 20 | SH-3 | 2 | 100 | SH-3 PET | 3 6 | 50 50 | 218 | 3 | 185 | 3 | 8.1 | 200 |
| Ex. 3 | heat bonding | 20 | SH-4 | 2 | 100 | SH-4 PET | 3 6 | 50 50 | 163 | 2 | 225 | 3 | 9.1 | 200 |
| Comp. Ex. 2 | heat bonding | 20 | SH-5 | 2 | 100 | SH-5 PET | 3 6 | 50 50 | 73 | 2 | 291 | 3 | 8.0 | 200 |
| Comp. Ex. 3 | interlocking with liquid | 20 | SH-4 PET | 2 2 | 0 100 | | | | 231 | 2 | 0 | not bonded | 4.7 | 200 |
| Ex. 4 | interlocking with liquid | 20 | SH-4 PET | 2 2 | 5 95 | | | | 225 | 2 | 38 | 3 | 5.5 | 200 |
| Ex. 5 | interlocking with liquid | 20 | SH-4 PET | 2 2 | 10 90 | | | | 229 | 2 | 51 | 3 | 5.9 | 200 |
| Ex. 6 | interlocking with liquid | 20 | SH-4 PET | 2 2 | 50 50 | | | | 193 | 3 | 108 | 3 | 7.0 | 200 |
| Ex. 7 | interlocking with liquid | 20 | SH-4 PET | 2 2 | 90 10 | | | | 185 | 3 | 264 | 3 | 9.5 | 200 |
| Comp. Ex. 4 | interlocking with liquid | 20 | NBF PET | 2 2 | 10 90 | | | | 229 | 2 | 35 | 2 | | 200 |
| Comp. Ex. 5 | interlocking with liquid | 20 | NBF PET | 2 2 | 50 50 | | | | 201 | 2 | 42 | 1 | 7.7 | 200 |
| Ex. 8 | heat bonding | 20 | SP-4 | 2 | 100 | SP-4 PET | 3 6 | 50 50 | 202 | 3 | 218 | 3 | 7.7 | 200 |
| Ex. 9 | interlocking with liquid | 20 | SP-4 PET | 2 2 | 50 50 | | | | 174 | 3 | 162 | 3 | 6.8 | 200 |
| Comp. Ex. 6 | heat bonding | 20 | PET | 2 | 100 | | | | 218 | 3 | 0 | not bonded | 4.3 | 200 |
| Ex. 10 | heat bonding | 20 | SH-4 | 2 | 100 | SH-4 PET | 3 6 | 50 50 | 163 | 3 | 62 | 3 | 5.8 | 140 |
| Ex. 11 | heat bonding | 20 | SH-6 | 3 | 100 | SH-6 PET | 3 6 | 50 50 | 163 | 3 | 59 | 2 | 5.7 | 130 |

TABLE 3

| No. of Ex. or Comp. Ex. | Fixing process of web. | Non-woven fabric | | | | | | | | | | Absorbent article | | |
|---|---|---|---|---|---|---|---|---|---|---|---|---|---|---|
| | | Basis weight (g/m²) | Surface layer | | | Inside layer | | | Tensile strength (g/50 mm) | Falling out of fuzz (rank) | Bond*1 strength (g/30 mm) | State of*1 bonded area (rank) | Absorption*1 capacity under dynamic condition (g) | Processing temperature (°C.) |
| | | | Fiber | Fineness (denier) | Content (%) | Fiber | Fineness (denier) | Content (%) | | | | | | |
| Comp. Ex. 7 | heat bonding | 20 | SH-4 / NBF | 2 / 2 | 0 / 100 | SH-4 / PET | 3 / 6 | 50 / 50 | 265 | 3 | less than 10 (160) | 1 (160) | — | 160–165 |
| Ex. 12 | heat bonding | 20 | SH-4 / NBF | 2 / 2 | 5 / 95 | SH-4 / PET | 3 / 6 | 50 / 50 | 260 | 3 | 31 (170) | 3 (170) | 5.5 (170) | 160–175 |
| Ex. 13 | heat bonding | 20 | SH-4 / NBF | 2 / 2 | 10 / 90 | SH-4 / PET | 3 / 6 | 50 / 50 | 256 | 3 | 90 (170) | 3 (170) | 5.4 (170) | 150–180 |
| Ex. 14 | heat bonding | 20 | SH-4 / NBF | 2 / 2 | 50 / 50 | SH-4 / PET | 3 / 6 | 50 / 50 | 238 | 3 | 184 (190) | 3 (190) | 7 (190) | 150–200 |
| Ex. 15 | heat bonding | 20 | SH-4 / NBF | 2 / 2 | 90 / 10 | SH-4 / PET | 3 / 6 | 50 / 50 | 210 | 3 | 256 (200) | 3 (200) | 8.1 (200) | 145–240 |
| Comp. Ex. 8 | heat bonding | 20 | PET / NBF | 2 / 2 | 10 / 90 | SH-4 / PET | 3 / 6 | 50 / 50 | 87 | 2 | 52 (165) | 1 (165) | 4.3 (165) | 160–170 |
| Comp. Ex. 9 | heat bonding | 20 | PET / NBF | 2 / 2 | 50 / 50 | SH-4 / PET | 3 / 6 | 50 / 50 | 55 | 1 | 29 (165) | 1 (165) | 4.4 (165) | 160–190 |

(Note)*1 The bond strength, state of bonded area and absorption capacity under dynamic condition were determined by using the absorbent articles each processed at the temperature shown in parentheses.

EFFECT OF THE INVENTION

It is apparent from the results of Examples 1 to 11 that the non-woven fabric according to the present invention can form an absorbent article having high bond strength and the bonded area of an excellent state. Further, it is also apparent that the absorbent article produced by heat-bonding the non-woven fabric according to the present invention to the absorbent layer exhibits high absorption capacity. Furthermore, the bonded area of the absorbent articles of Examples 10 and 11 hardly contained filmy area and was very excellent in touch.

However, the bonded area of the absorbent article of Example 11 wherein the second resin component of the conjugate fiber had a melting point near that of the laminating film used partially exhibited low bond strength, thus being incomplete, though no breaking was observed.

In Comparative Example 1, the second resin component of the conjugate fiber had a melt flow rate of less than 10, so that it exhibited insufficient fluidity when melted. Accordingly, the bond strength was low. On the contrary, in Comparative Example 2, the second resin component of the conjugate fiber had a melt flow rate exceeding 50, so that the non-woven fabric exhibited low tensile strength. In Comparative Examples 3 and 6, all of the fiber constituting the non-woven fabric had the same melting point, so that only the polyethylene layer of the leakproof paper was melted at a sealing temperature lower than the melting point of the fiber (PET) used to form no bonding. In Comparative Examples 4 and 5, the difference in melting point between the two fibers constituting the conjugate fiber was smaller than 100° C., so that significant adhering of the fiber to a sealer was observed.

Examples 12 to 15 shows that the non-woven fabric produced by dry heat-bonding process according to the present invention exhibits improved thermoprocessability, i.e., enlarged processing temperature range without causing lowering in the strength nor increase in the falling out of fuzz.

In Comparative Example 7, the non-woven fabric was not problematic in strength and falling out of fuzz. But, the adhering of the fabric to a sealer was too significant to carry out the sealing. In Comparative Examples 8 and 9 wherein the blending of PET was carried out with the purpose of inhibiting the adhering, the resulting non-woven fabric exhibited remarkably lowered strength and significant falling out of fuzz.

All of the absorbent articles of Examples according to the present invention exhibited absorption capacity remarkably higher than that of the absorbent article of Comparative Example 3 or 6 wherein the non-woven fabric was not bonded to the absorbent layer by sealing or Comparative Example 1 wherein the bond strength was very low.

In Comparative Examples 4, 5 and 7, the adhering of the non-woven fabric to a sealer or the breaking of the bonded area occurred in the sealing, so that the obtained article could not stand use as an absorbent article.

In Comparative Examples 8 and 9, the strength of the non-woven fabric was low, so that the non-woven fabric of the absorbent article after the measurement of absorption capacity under a dynamic condition was broken and the absorption capacity was low.

What is claimed is:

1. An absorbent article which comprises:
   an absorbent layer capable of absorbing a liquid;
   a leakproof layer disposed on one side of said absorbent layer; and
   a non-woven fabric layer disposed on the opposite side of said absorbent layer from said leakproof layer and having a surface layer which comprises 50 to 100% by weight of conjugate fibers, wherein said conjugate fibers comprise a first resin and a second resin, wherein said first resin has a melting point that is higher by at least 100° C. than that of said second resin, and wherein said second resin has a melt flow rate of 10 to 50.

2. An absorbent article as claimed in claim 1, wherein said first resin has a melting point of 200° C. or higher and said second resin has a melting point of 180° C. or lower.

3. An absorbent article as claimed in claim 1, wherein the weight ratio of said first resin to said second resin in said conjugate fibers ranges from 70:30 to 30:70.

4. An absorbent article as claimed in claim 1, wherein said second resin has a melt flow rate of 20 to 50.

5. An absorbent article as claimed in claim 1, wherein all of said surface layer of said non-woven fabric layer has been formed from said conjugate fibers.

6. An absorbent article as claimed in claim 1, wherein said non-woven fabric layer and said leakproof layer are partially fastened to each other by heat bonding.

7. An absorbent article as claimed in claim 2, wherein the weight ratio of said first resin to said second resin in said conjugate fibers ranges from 70:30 to 30:70.

8. An absorbent article as claimed in claim 7, wherein said second resin has a melt flow rate of 20 to 50.

9. An absorbent article as claimed in claim 8, wherein all of said surface layer of said non-woven fabric layer has been formed from said conjugate fibers.

10. An absorbent article as claimed in claim 9, wherein said non-woven fabric layer and said leakproof layer are partially fastened to each other by heat bonding.

11. An absorbent article as claimed in claim 1, wherein said conjugate fibers comprise 50 to 0% by weight of a fiber having a melting point near that of said first resin.

12. An absorbent article as claimed in claim 10, wherein said conjugate fibers comprise 50 to 0% by weight of a fiber having a melting point near that of said first resin.

13. An absorbent article as claimed in claim 1, wherein said conjugate fibers have a size of 1.5 to 6 denier.

14. An absorbent article as claimed in claim 12, wherein said conjugate fibers have a size of 1.5 to 6 denier.

15. An absorbent article as claimed in claim 1, wherein said surface layer of said conjugate fibers are treated so as to be suitably hydrophilic.

16. An absorbent article as claimed in claim 14, wherein said surface layer of said conjugate fibers are treated so as to be suitably hydrophilic.

17. An absorbent article as claimed in claim 1, wherein said first and second resins of said conjugate fibers have a core-sheath structure which includes a core of said first resin and a sheath of said second resin.

18. An asorbent article as claimed in claim 1, wherein said first and second resins of said conjugate fibers have a sea-island structure which includes fine filaments of said first resin dispersed in said second resin.

* * * * *